United States Patent
Schneider et al.

(10) Patent No.: US 9,549,755 B2
(45) Date of Patent: Jan. 24, 2017

(54) CUTTER FOR TISSUE-REMOVING CATHETER

(71) Applicant: Covidien LP, Mansfield, MA (US)

(72) Inventors: Lucas Schneider, Champlin, MN (US); Benjamin Fruland, Blaine, MN (US)

(73) Assignee: Covidien LP, Mansfield, MA (US)

( * ) Notice: Subject to any disclaimer, the term of this patent is extended or adjusted under 35 U.S.C. 154(b) by 467 days.

(21) Appl. No.: 14/102,029

(22) Filed: Dec. 10, 2013

(65) Prior Publication Data

US 2014/0171987 A1 Jun. 19, 2014

Related U.S. Application Data

(60) Provisional application No. 61/736,165, filed on Dec. 12, 2012.

(51) Int. Cl.
| | | |
|---|---|---|
| *A61B 17/3207* | (2006.01) | |
| *A61B 17/22* | (2006.01) | |
| *A61B 17/32* | (2006.01) | |
| *A61B 17/00* | (2006.01) | |

(52) U.S. Cl.
CPC . *A61B 17/320758* (2013.01); *A61B 17/32002* (2013.01); *A61B 17/3207* (2013.01); *A61B 17/320783* (2013.01); *A61B 2017/00685* (2013.01); *A61B 2017/320775* (2013.01)

(58) Field of Classification Search
CPC ............ A61B 17/3207; A61B 17/320783; A61B 2017/00685; A61B 17/320758; A61B 2017/320775; A61B 17/32002
See application file for complete search history.

(56) References Cited

U.S. PATENT DOCUMENTS

| | | |
|---|---|---|
| 4,290,427 A | 9/1981 | Chin |
| 4,631,052 A | 12/1986 | Kensey |
| 4,765,332 A | 8/1988 | Fischell et al. |
| 4,790,813 A | 12/1988 | Kensey |
| 4,926,858 A | 5/1990 | Gifford, III et al. |
| 4,950,277 A | 8/1990 | Farr |
| 5,026,383 A | 6/1991 | Nobles |
| 5,085,662 A | 2/1992 | Willard |
| 5,100,424 A | 3/1992 | Jang et al. |
| 5,123,904 A | 6/1992 | Shimomura et al. |

(Continued)

OTHER PUBLICATIONS

International Search Report and Written Opinion of the International Searching Authority for PCT/US2013/073517, Mar. 7, 2014, 11 pages, Rijswijk Netherlands.

*Primary Examiner* — Jing Ou

(57) ABSTRACT

A rotatable cutter for a tissue-removing catheter includes a central hub, flutes spaced apart from one another around the circumference of the central hub, and arcuate cutting members. Each cutting member includes an arcuate cutting edge extending along an arc length of the cutting member for cutting tissue as the cutter is rotated. A raised element of each cutting member has a leading cutting edge at a leading end of the distal cutting member for cutting tissue as the cutter is rotated. A clearance portion of each cutting member is recessed, relative to the longitudinal axis of the cutter, from the raised element and extends from the raised element to a trailing end of the cutting member to provide clearance for the leading cutting edge of an adjacent and opposing distal cutting member.

21 Claims, 13 Drawing Sheets

(56) References Cited

U.S. PATENT DOCUMENTS

| | | |
|---|---|---|
| 5,176,693 A | 1/1993 | Pannek, Jr. |
| 5,192,291 A | 3/1993 | Pannek, Jr. |
| 5,226,909 A | 7/1993 | Evans et al. |
| 5,242,460 A | 9/1993 | Klein et al. |
| 5,350,390 A | 9/1994 | Sher |
| 5,507,760 A | 4/1996 | Wynne et al. |
| 5,507,795 A | 4/1996 | Chiang et al. |
| 5,512,044 A * | 4/1996 | Duer ............ A61B 17/32075 604/22 |
| 5,556,408 A | 9/1996 | Farhat |
| 5,569,277 A | 10/1996 | Evans et al. |
| 5,601,580 A | 2/1997 | Goldberg et al. |
| 5,620,456 A | 4/1997 | Sauer et al. |
| 5,632,755 A * | 5/1997 | Nordgren ........ A61B 17/32075 604/22 |
| 5,776,156 A | 7/1998 | Shikhman |
| 5,857,982 A | 1/1999 | Milliman et al. |
| 6,053,923 A | 4/2000 | Veca et al. |
| 6,068,603 A | 5/2000 | Suziki |
| 6,110,127 A | 8/2000 | Suziki |
| 6,428,539 B1 | 8/2002 | Baxter et al. |
| 6,503,263 B2 | 1/2003 | Adams |
| RE38,018 E | 3/2003 | Anctil et al. |
| 6,579,298 B1 | 6/2003 | Bruneau et al. |
| RE38,335 E | 11/2003 | Aust et al. |
| 6,656,195 B2 * | 12/2003 | Peters ............ A61B 17/32002 606/159 |
| 7,329,267 B2 | 2/2008 | Weber |
| 7,344,546 B2 | 3/2008 | Wulfmann et al. |
| 7,485,125 B2 | 2/2009 | Sjostrom |
| 7,520,886 B2 | 4/2009 | Surti |
| 7,635,340 B2 | 12/2009 | Vetter et al. |
| 7,699,790 B2 | 4/2010 | Simpson |
| 7,862,518 B2 | 1/2011 | Parihar |
| 7,918,803 B2 | 4/2011 | Ritchart et al. |
| 7,927,784 B2 | 4/2011 | Simpson |
| 7,951,161 B2 | 5/2011 | Bonnette et al. |
| 7,981,128 B2 | 7/2011 | To et al. |
| 8,012,164 B1 | 9/2011 | Donohoe et al. |
| 8,052,704 B2 | 11/2011 | Olson |
| 8,062,316 B2 | 11/2011 | Patel et al. |
| 8,070,762 B2 | 12/2011 | Escudero et al. |
| 2003/0078606 A1 * | 4/2003 | Lafontaine ......... A61B 17/3207 606/159 |
| 2004/0006358 A1 | 1/2004 | Wulfman et al. |
| 2006/0229646 A1 * | 10/2006 | Sparks ............ A61B 17/32075 606/159 |
| 2007/0055259 A1 | 3/2007 | Norton et al. |
| 2007/0276419 A1 | 11/2007 | Rosenthal |
| 2007/0282358 A1 | 12/2007 | Remiszewski et al. |
| 2008/0004643 A1 * | 1/2008 | To ................ A61B 17/32075 606/159 |
| 2008/0045986 A1 | 2/2008 | To et al. |
| 2008/0065124 A1 | 3/2008 | Olson |
| 2008/0140104 A1 | 6/2008 | Bender et al. |
| 2010/0049225 A1 * | 2/2010 | To ................ A61B 17/32075 606/159 |
| 2010/0198240 A1 | 8/2010 | Simpson et al. |
| 2011/0004107 A1 | 1/2011 | Rosenthal et al. |
| 2011/0087258 A1 | 4/2011 | Sluss |
| 2011/0130777 A1 | 6/2011 | Zhang et al. |
| 2011/0144673 A1 | 6/2011 | Zhang et al. |
| 2011/0152906 A1 | 6/2011 | Escudero et al. |
| 2011/0190801 A1 | 8/2011 | Mark et al. |
| 2011/0301626 A1 | 12/2011 | To et al. |
| 2011/0306995 A1 | 12/2011 | Moberg |
| 2013/0096587 A1 * | 4/2013 | Smith ............ A61B 17/32075 606/159 |

* cited by examiner

CUTTER FOR TISSUE-REMOVING CATHETER

CROSS-REFERENCE TO RELATED APPLICATIONS

The present application claims priority to U.S. Provisional Application Ser. No. 61/736,165, filed Dec. 12, 2012, the entirety of which is hereby incorporated by reference.

FIELD OF THE DISCLOSURE

The present invention generally relates to a cutter for a tissue-removing catheter.

BACKGROUND OF THE DISCLOSURE

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

It is desirous to provide catheters which can access small, tortuous regions of body lumens and which can remove tissue and/or other occluding materials from within body lumens in a controlled fashion. In one instance, it may be desired to provide atherectomy catheters which can facilitate capturing atheromatous materials. The catheters and methods for use in a variety of body lumens, including but not limited to coronary, peripheral, and other arteries, and other body lumens.

SUMMARY OF THE DISCLOSURE

A rotatable cutter for a tissue-removing catheter includes a central hub, flutes spaced apart from one another around the circumference of the central hub, and arcuate cutting members. Each cutting member includes an arcuate cutting edge extending along an arc length of the cutting member for cutting tissue as the cutter is rotated. A raised element of each cutting member has a leading cutting edge at a leading end of the distal cutting member for cutting tissue as the cutter is rotated. A clearance portion of each cutting member is recessed, relative to the longitudinal axis of the cutter, from the raised element and extends from the raised element to a trailing end of the cutting member to provide clearance for the leading cutting edge of an adjacent and opposing distal cutting member.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
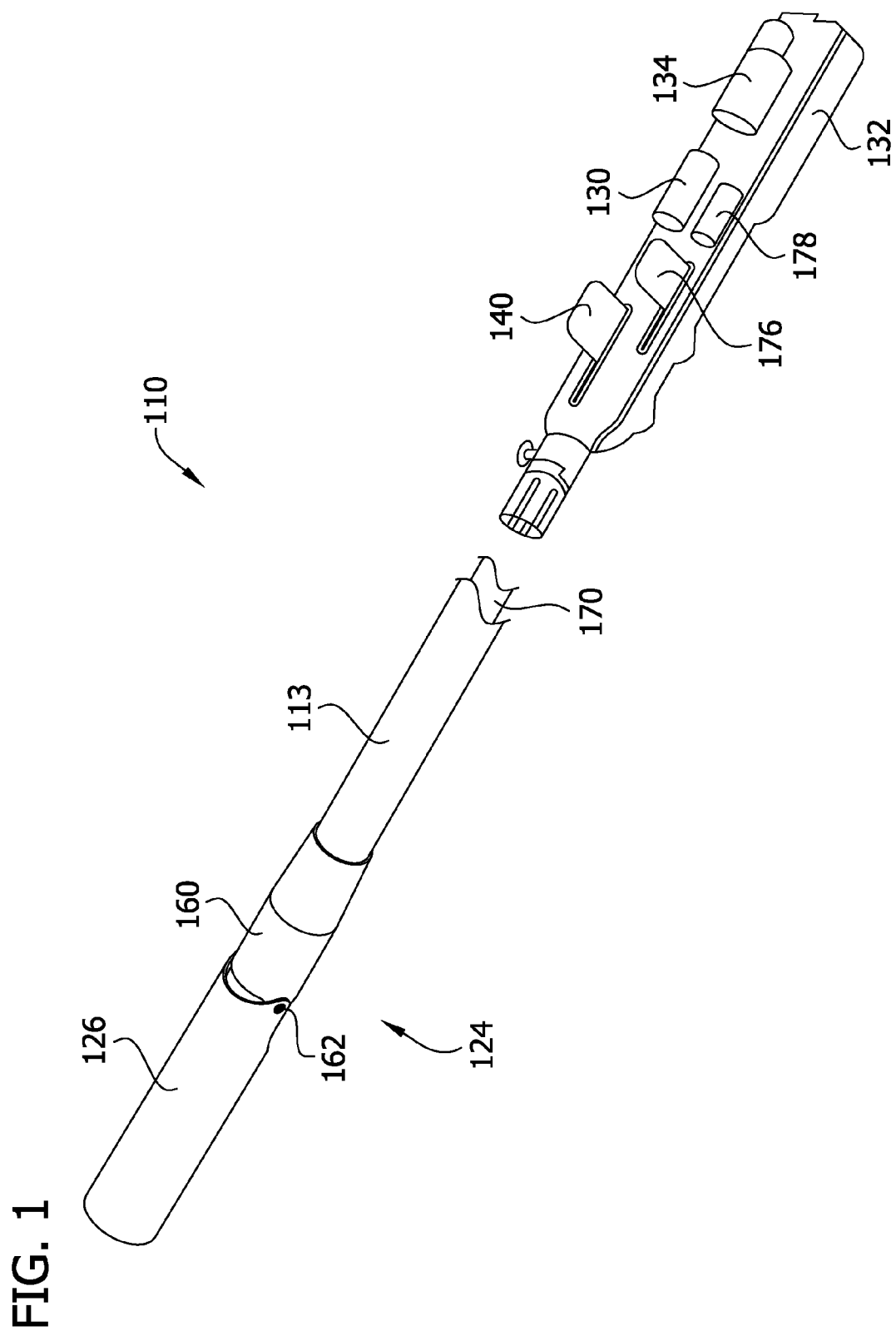
FIG. 1 is a fragmentary perspective of a first embodiment of a tissue-removing catheter.

Referring now to the drawings, a tissue-removing catheter is generally indicated at reference numeral 110. The tissue-removing catheter includes, among other components, a rotatable cutter, generally indicated at 112, for removing tissue from a body lumen. The illustrated tissue-removing catheter is suitable for removing tissue from a body lumen, and are particularly suitable for removing (i.e., excising) plaque tissue from a vessel (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Referring to FIGS. 1-4, the illustrated catheter 110 includes an elongate tubular catheter body 113 having opposite proximal and distal ends, a central longitudinal axis $LA_1$ (FIG. 3) extending between the distal and proximal ends, and an internal tissue-transport passage 114 (FIGS. 3 and 4) extending generally along the longitudinal axis of the body. The catheter body 113 is configured (e.g., sized and shaped) for intravascular introduction into the target artery, although as explained above, the catheter body may be configured for intraluminal introduction into other target body lumens other than a target artery. Although not illustrated, the catheter 110 may be configured for introduction of the catheter body 113 over a guidewire to a target site within the vasculature. In particular, the catheter 110 may be configured for "over-the-wire" introduction when a guidewire channel extends fully through the catheter body 113 or for "rapid exchange" introduction where the guidewire channel extends only through a distal portion of the catheter body. In other cases, it may be possible to provide a fixed or integral coil tip or guidewire tip on the distal portion of the catheter 110 or even dispense with the guidewire entirely. Moreover, a flexible distal tip (not shown) may be secured to the distal end of the illustrated catheter to facilitate insertion of the catheter. For convenience of illustration, guidewires will not be shown in any embodiment, but it should be appreciated that they can be incorporated into any of these embodiments.

The dimensions and other physical characteristics of the catheter body 113 may vary depending on the artery (or other body lumen) of the subject which is to be accessed. The catheter body 113 is generally flexible and may in one embodiment have a length in the range from 50 cm to 200 cm and an outer diameter in the range from 1 French to 12 French (0.33 mm: 1 French), such as from 3 French to 9 French. The catheter body 113 may be composed of an organic polymer which is fabricated by extrusion techniques. Suitable polymers include polyvinylchloride, polyurethanes, polyesters, polytetrafluoroethylenes (PTFE), silicone rubbers, natural rubbers, and the like. Optionally, the catheter body 113 may be reinforced with a braid, helical wires, coils, axial filaments, or the like, in order to increase rotational strength, column strength, toughness, pushability, and the like. For example, the catheter body 113 may include a torque tube, as is generally known in the art. The outer diameter of the catheter body 113 can be modified by heat expansion and shrinkage using conventional techniques. It will be appreciated that the construction and dimensions of the catheter body may be other than described without departing from the scope of the present invention.

The catheter body 113 of the present embodiment may include an urging mechanism (not shown) to urge the cutter into engagement with the arterial wall during treatment. For example, the urging mechanism may comprise a portion of the catheter body 113 adjacent to and proximal of the cutter 112 that is biased to (e.g., permanently deformed in) a double-bent or double-curved shape to urge the cutter toward a wall of a body lumen to enhance treatment. A suitable urging mechanism is disclosed in U.S. Pat. No. 7,708,749, the entirety of which is hereby incorporated by reference. In other embodiments, the urging mechanism may take many other suitable forms. The catheter may not include an urging mechanism without departing from the scope of the present invention.

The rotatable cutter 112 is operatively connected to the distal end of the catheter body 113 for removing tissue from an arterial wall. A driveshaft 120, which includes an external helical thread 122, drives rotation of the cutter 112 and also transports or moves removed tissue proximally within the tissue-transport passage 114 of the catheter body 113. The body of the driveshaft 120 (i.e., the part of the driveshaft not including the thread 122) is generally flexible and may be formed from one or more coils (e.g., stainless steel coil(s)), or a torque tube (e.g., a polyimide tube with a layer of braided stainless steel wire embedded therein). The body of the driveshaft 120 may have a very high torsional stiffness and sufficient tensile strength, but which is generally laterally flexible. Depending upon the desired torque transmission, diameter and flexibility, any of a variety of other materials and constructions may also be used.

As shown in FIG. 1, the driveshaft 120 is operatively connected to a cutter driver 130 (e.g., a cutter motor) in a handle 132 for imparting rotation of the driveshaft. The handle 132 also includes an actuator 140 (e.g., a lever) for activating the cutter driver 130 and a power source 134 for supplying power to the cutter driver. A deployment mechanism, generally indicated at 124, comprises a cutter housing 126 that is configurable between a closed position (FIGS. 1 and 3), in which the cutter 112 is not exposed for cutting, and an open position (FIG. 4), in which the cutter is exposed through a cutting window 159 defined by the cutter housing.

Referring to FIGS. 1-4, a housing adaptor 160 is secured to the distal end of the catheter body 113. For purposes of this disclosure, the housing adaptor 160 is considered part of the catheter body 113. A proximal end portion of the cutter housing 126 is pivotably connected to the housing adaptor 160 by pins 162 (only one pin is visible in FIG. 1; the other pin is at a location diametrically opposite the visible pin). As explained below, the cutter housing 126 is selectively pivotable about the pins 162 for opening and closing the cutter housing.

Figure 2:
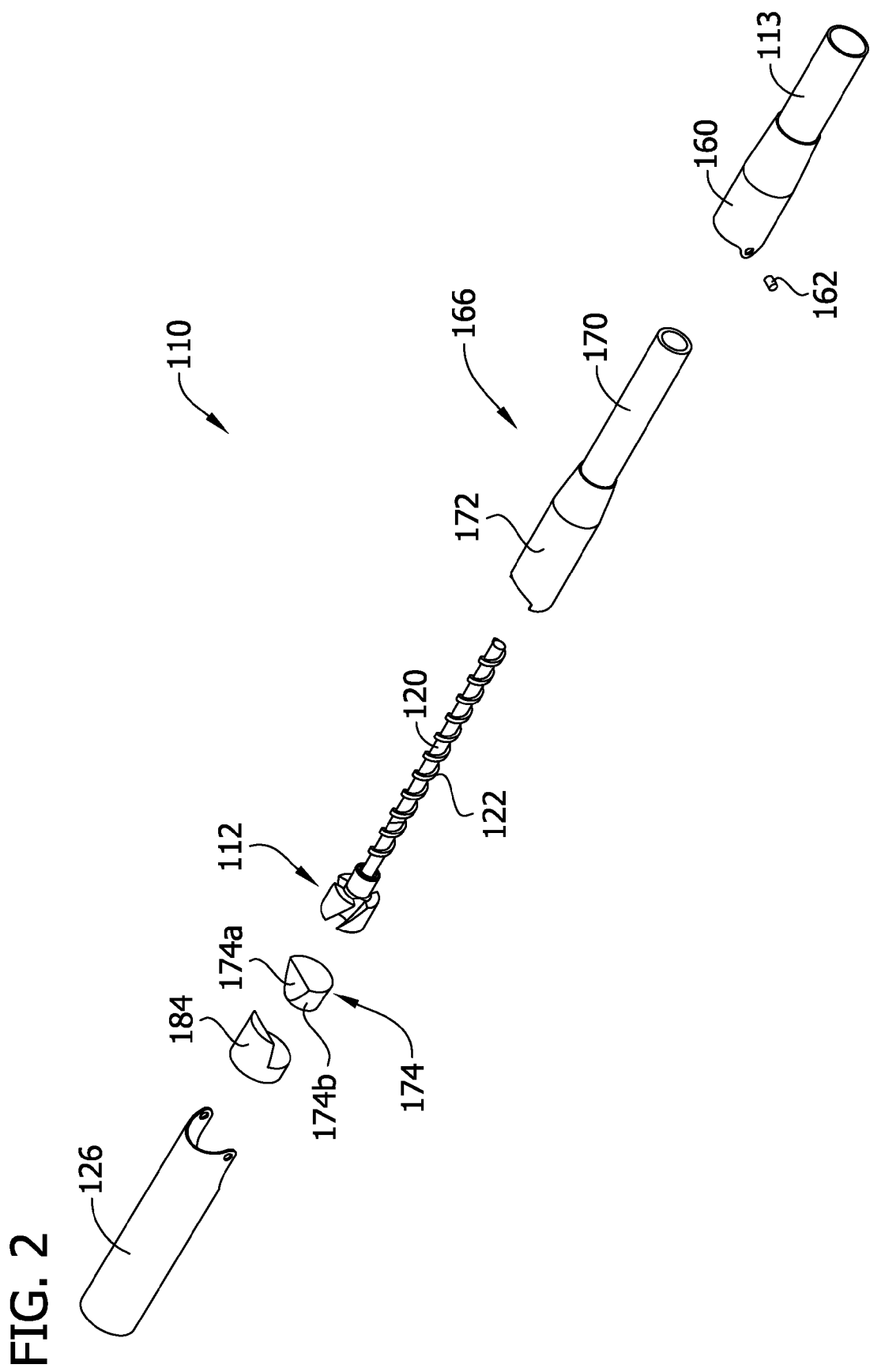
FIG. 2 is an enlarged exploded perspective of distal end portion of the tissue-removing catheter with a polymer jacket removed.
Figure 3:
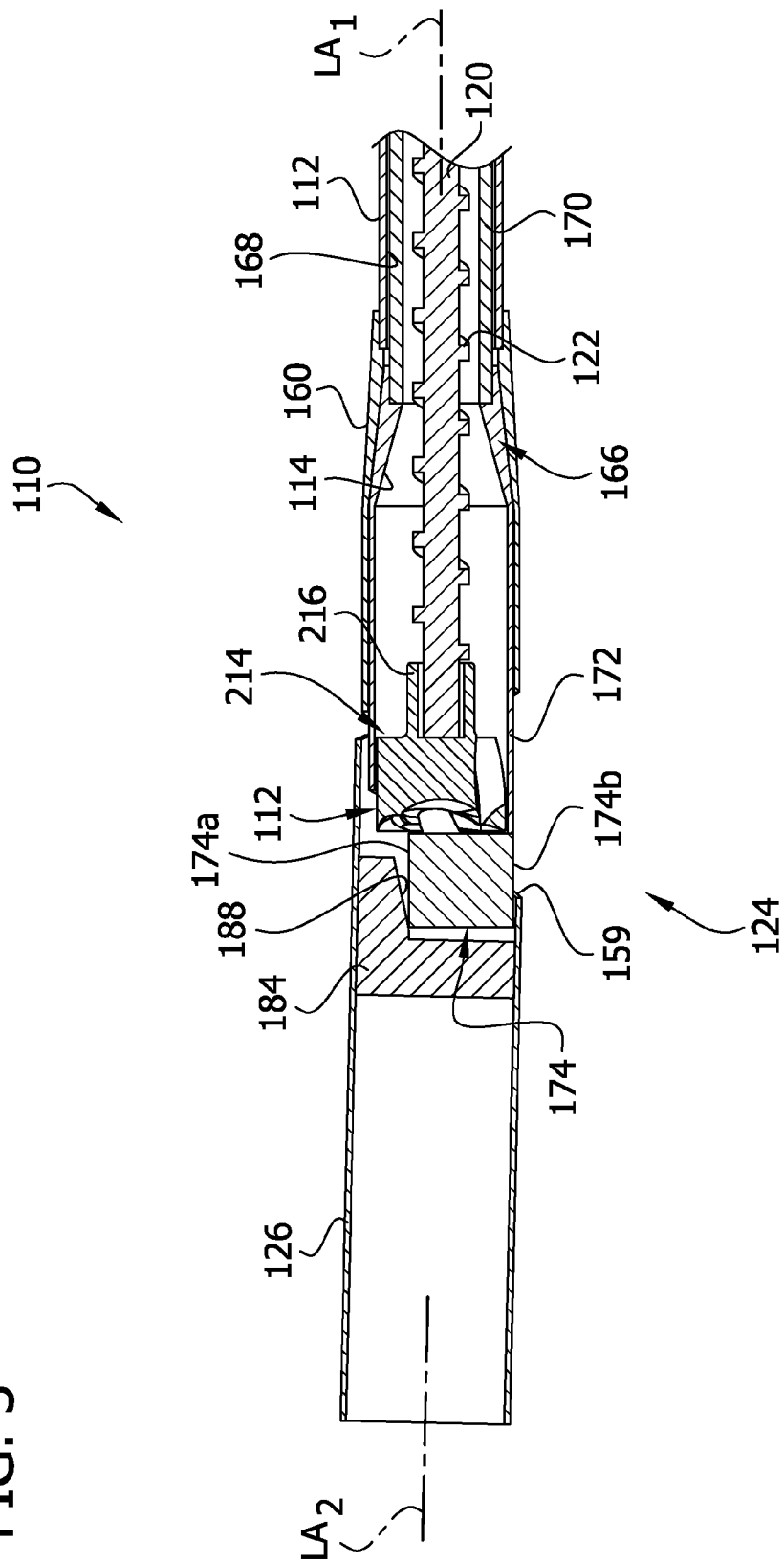
FIG. 3 is a longitudinal section of the distal end portion of the tissue-removing catheter.
Figure 4:
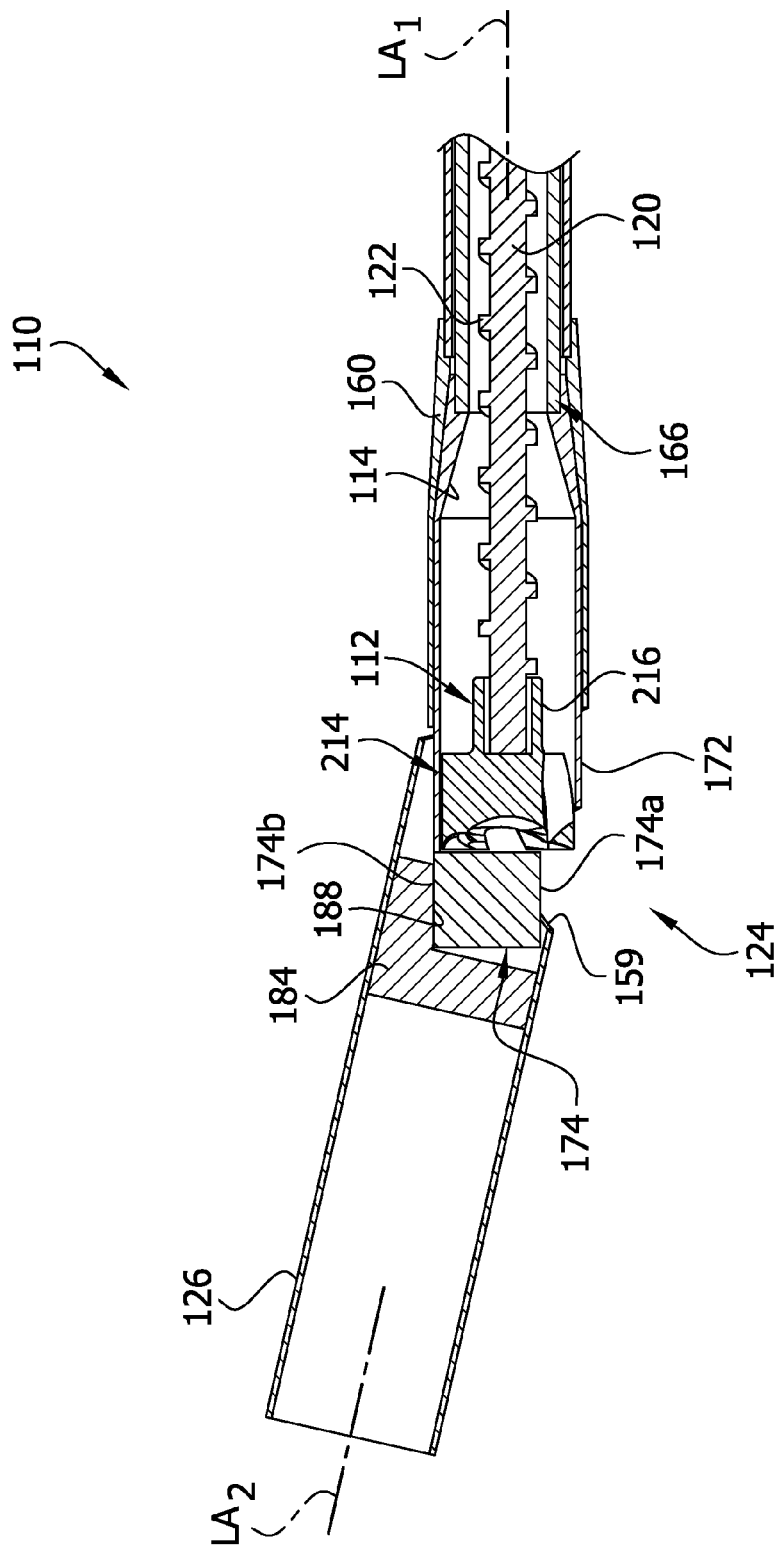
FIG. 4 is a longitudinal section of the distal end portion of the tissue-removing catheter, with the cutter of the tissue-removing catheter in a deployed, cutting position.

Referring to FIGS. 2-4, a cam shaft, generally indicated at 166, extends through a cam passage 168 extending longitudinally through the catheter body 113, including the housing adaptor 160. The cam shaft 166 includes a tubular torque shaft 170 (e.g., a torque tube), a cutter adaptor 172 fixedly secured to and extending longitudinally outward from a distal end of the torque shaft, and an eccentric 174 fixedly secured to a distal end of the cutter adaptor. The torque shaft 170 is rotatable about its longitudinal axis relative to the catheter body 113. A proximal end of the torque shaft 170 is operatively connected to the handle 132 for imparting rotation of the shaft about its longitudinal axis. In particular, referring to FIG. 1 the handle 132 may include an actuator 176 (e.g., a lever or knob) for imparting rotation to the torque shaft 170. In one example, the actuator 176 is a manual actuator for manually rotating the torque shaft 170. In another example, such as illustrated, the actuator 176 activates a cam motor 178 that is operatively connected to the torque shaft 170 to impart rotation to the torque shaft. The torque shaft 170 may be rotatable in other ways.

Rotation of the torque shaft 170 about its axis imparts rotation of the cutter adaptor 172 about the axis of the torque shaft, relative to the cutter 116 and the catheter body 113. The tissue-transport passage 114 is defined by interior surfaces of the cutter adaptor 172 and the torque shaft 168. In the illustrated embodiment, tissue cut by the cutter 112 travels through the cutter 112 and into the tissue-transport passage 114, where the removed tissue is picked up by the rotating driveshaft 120 and transported proximally within the catheter body 113.

Rotation of the torque shaft 170 about its axis also imparts rotation of the eccentric 174 about the axis of the torque shaft 170 relative to the cutter housing 126. The eccentric 174 interacts with a cam follower 184 secured to (e.g., secured within) the cutter housing 126 to drive opening and closing of the cutter housing. More specifically, when the cutter housing 126 is in the closed position, a generally flat surface 174a (e.g., a longitudinally truncated portion) opposes an engagement surface 188 of the cam follow 184, and an arcuate surface 174b of the eccentric is adjacent the cutter window 159. As the eccentric 174 rotates about the axis of the torque shaft 170, the engagement surface 188 of the cam follower 184 rides along an arcuate surface 174b of the eccentric, whereby the cutter housing 126 pivots or rotates about the hinge pins 162, away from the cutter 112 is exposed through the cutter window 159. When the eccentric 174 is rotated about 180 degrees from its position when the cutter housing 126 is closed, the flat surface 174a is adjacent the cutter window, and the cutter housing is fully open, as shown in FIG. 4. In the fully open position, a longitudinal axis $LA_2$ of the cutter housing 126 extends at an offset angle relative to the longitudinal axis $LA_1$ of the catheter body 113. This offset angle may measure from about 15 degrees to about 45 degrees, or from about 20 degrees to about 30 degrees. As shown in FIGS. 3 and 4, the radial extent of the flat surface 174a is less than that of the cutting edge 150 of the cutter 112, such that the eccentric does not cover the exposed portion of the cutting edge of the cutter when the cutter housing is in the open position. In one embodiment, amount by which the cutting edge 150 is exposed is adjustable by allowing the eccentric 174 to be rotated incrementally to different rotational positions, which would allow for selective adjustment of the offset angle. To close the cutter housing 126, the eccentric 174 is rotated to its initial position when the cutter housing is closed, such that the cutter housing pivots toward the cutter 112 about the pins 162.

It is understood that the catheter 110 may be of other configurations without departing from the scope of the present invention.

Referring to FIGS. 5-11, the rotatable cutter 112 has distal and proximal ends and a longitudinal axis $LA_3$ (FIG. 6) extending therebetween. The cutter 112 has a generally cylindrical body, generally indicated at 214, and a stem 216 (broadly, a driveshaft-connection portion) for connecting the cutter to a driveshaft (FIGS. 3 and 4), for rotating the cutter about its longitudinal axis $LA_3$. The cutter 112 may be formed as a single, one-piece construction, or may be formed from separate components secured to one another in a suitable manner, such as welding, soldering, adhesives, mechanical interference fit, threaded engagement and the like. As a non-limiting example, the cutter 112 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Figure 5:
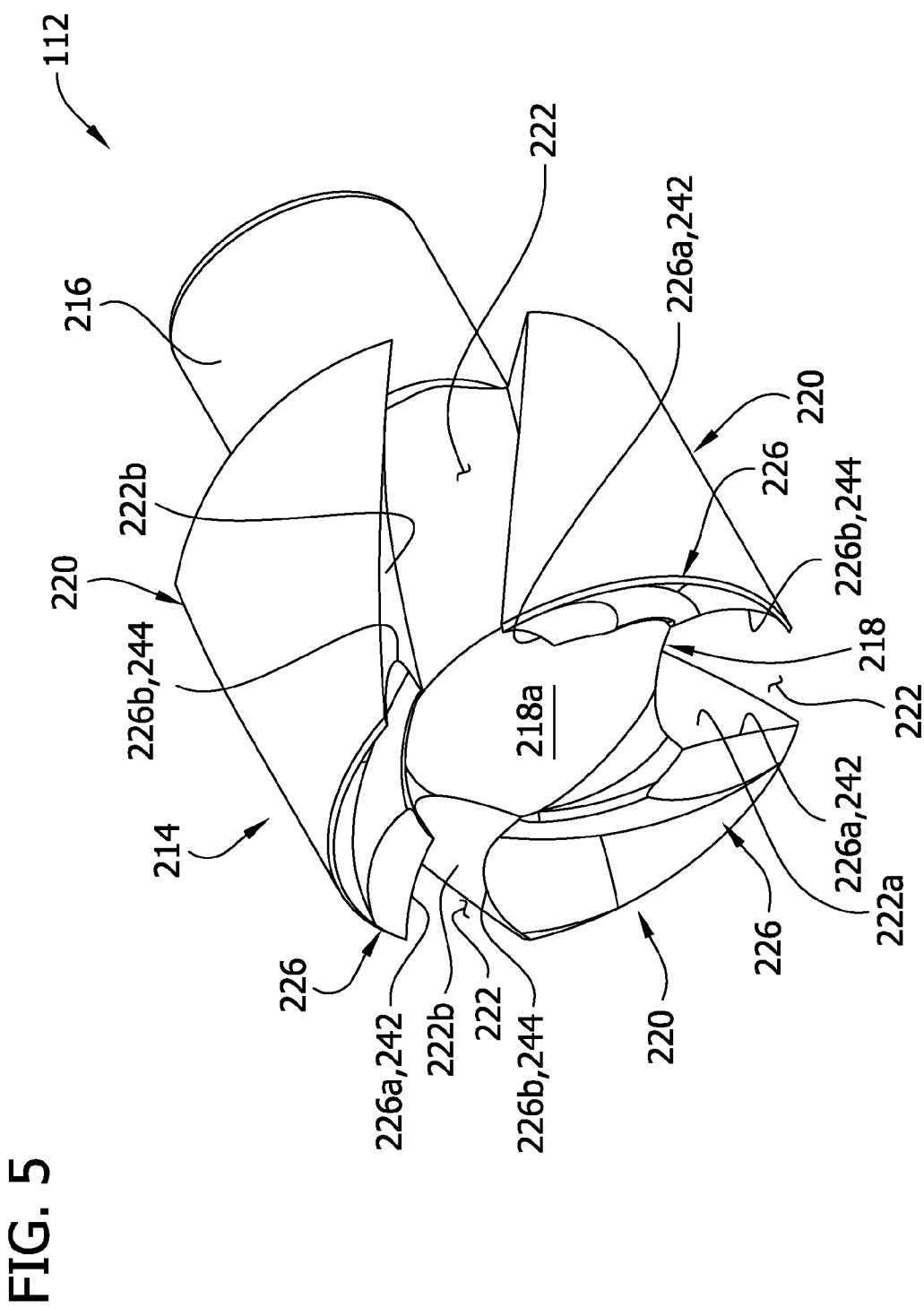
FIG. 5 is a perspective of a cutter of the tissue-removing catheter.
Figure 6:
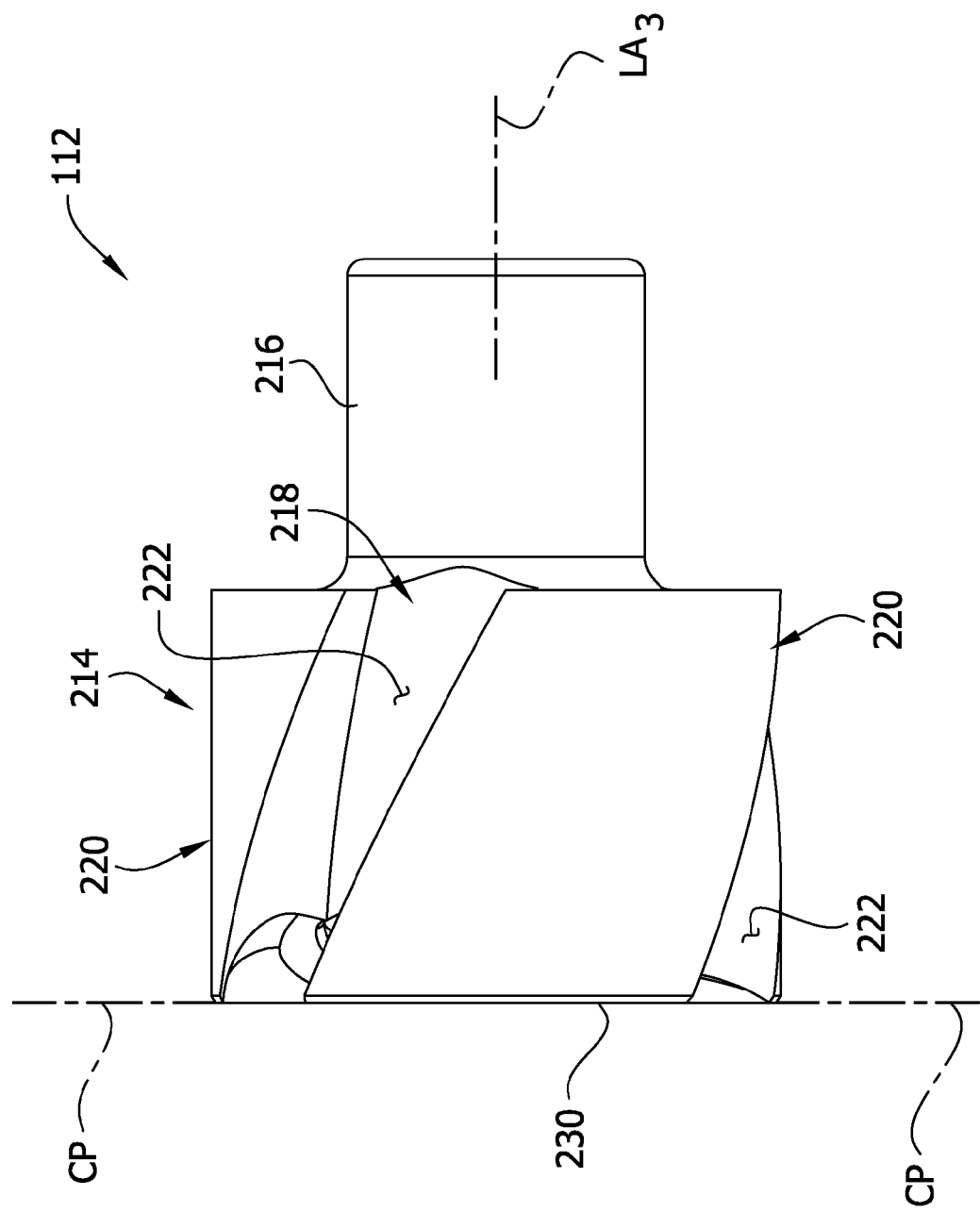
FIG. 6 is a side elevational view of the cutter.
Figure 7:
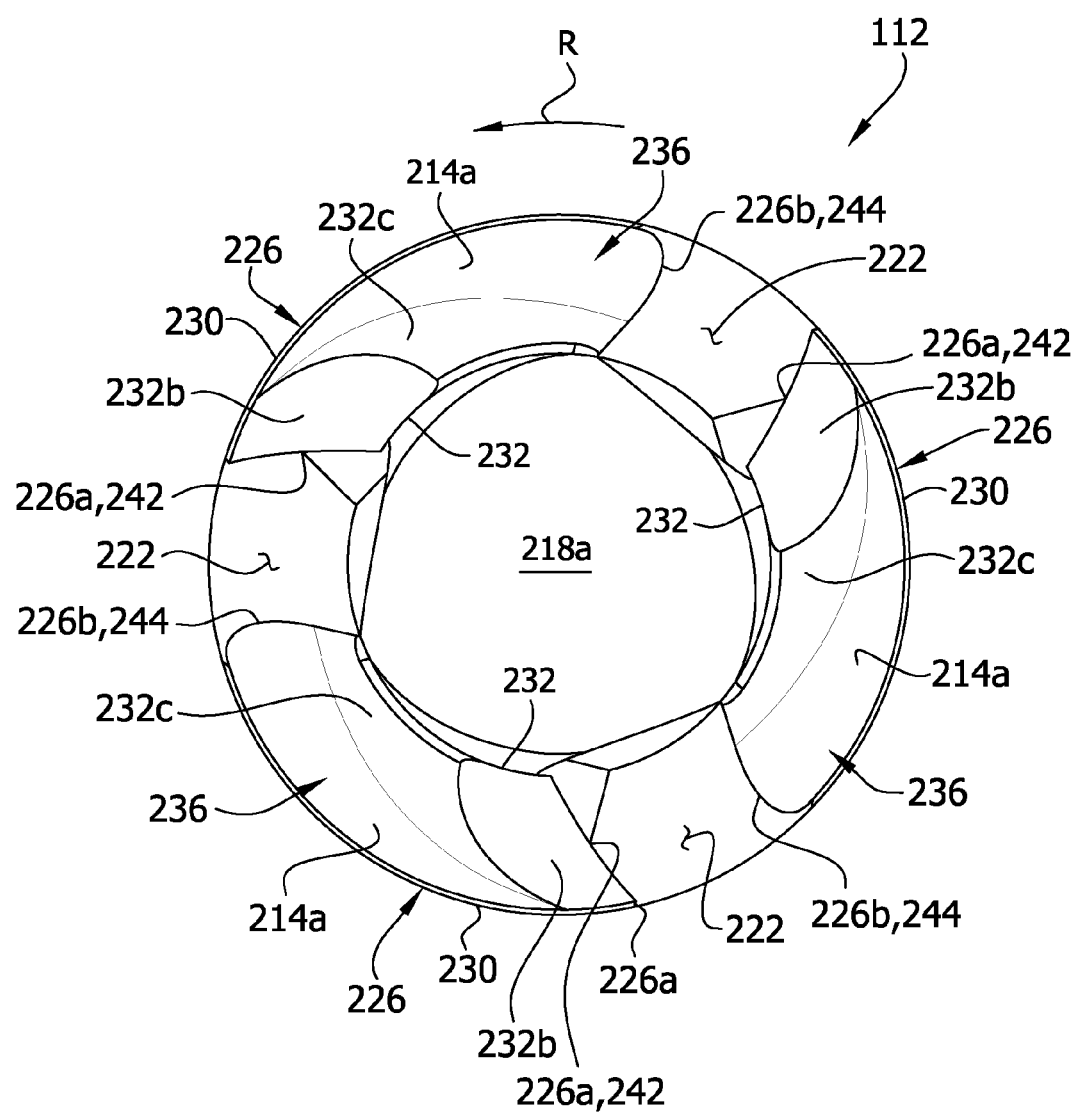
FIG. 7 is a front elevational view of the cutter.
Figure 7A:
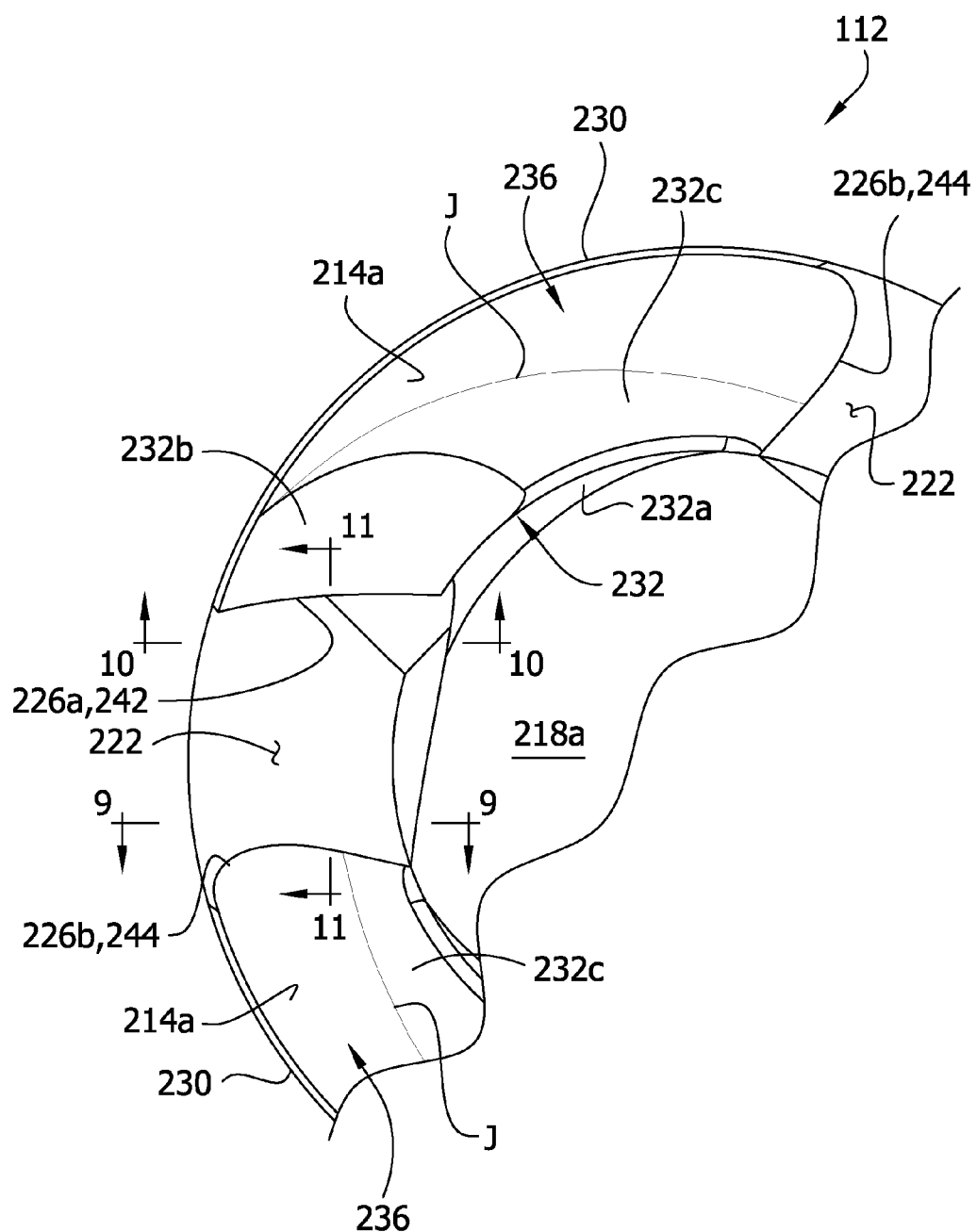
FIG. 7A is an enlarged, fragmentary view of FIG. 7.
Figure 8:
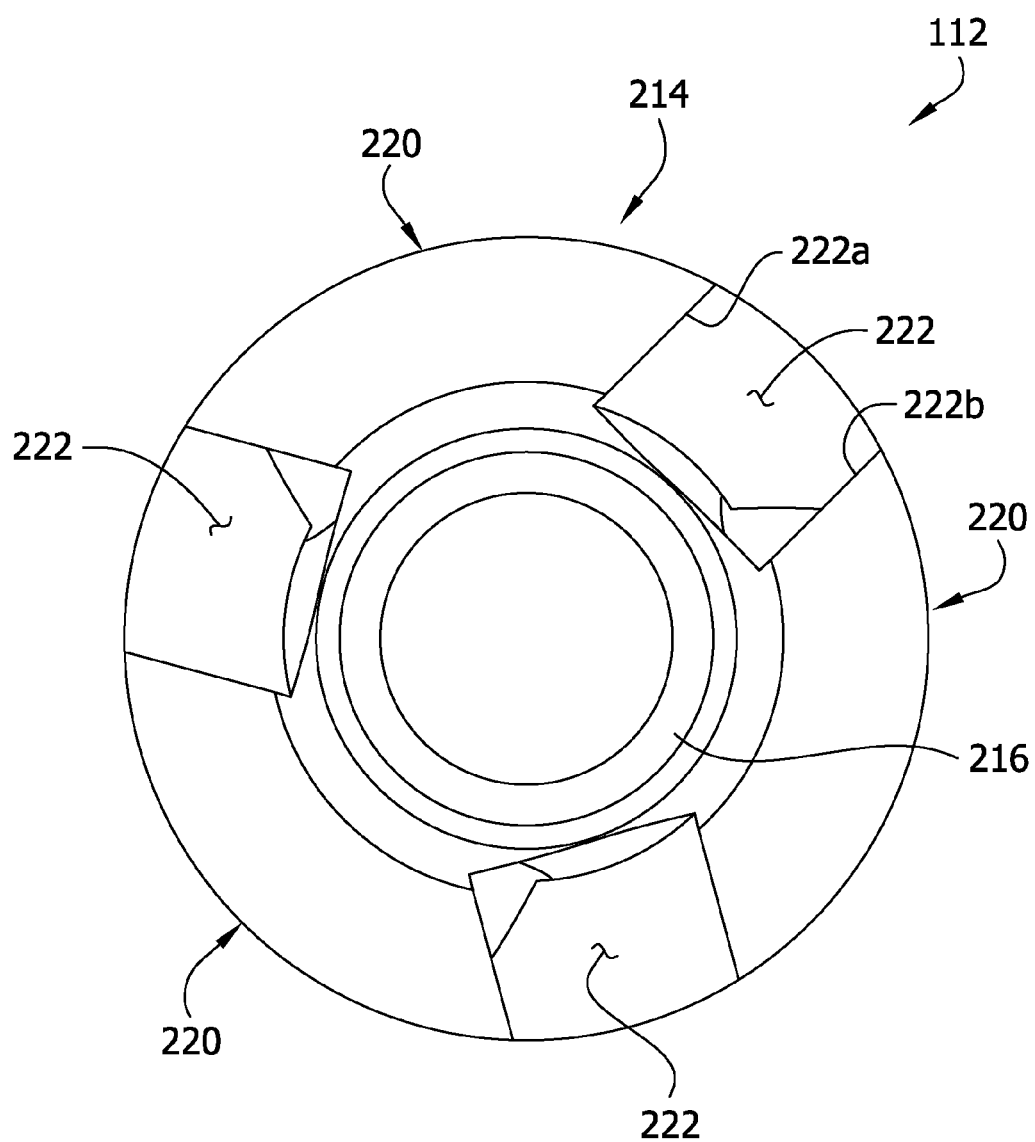
FIG. 8 is a rear elevational view of the cutter.
Figure 9:
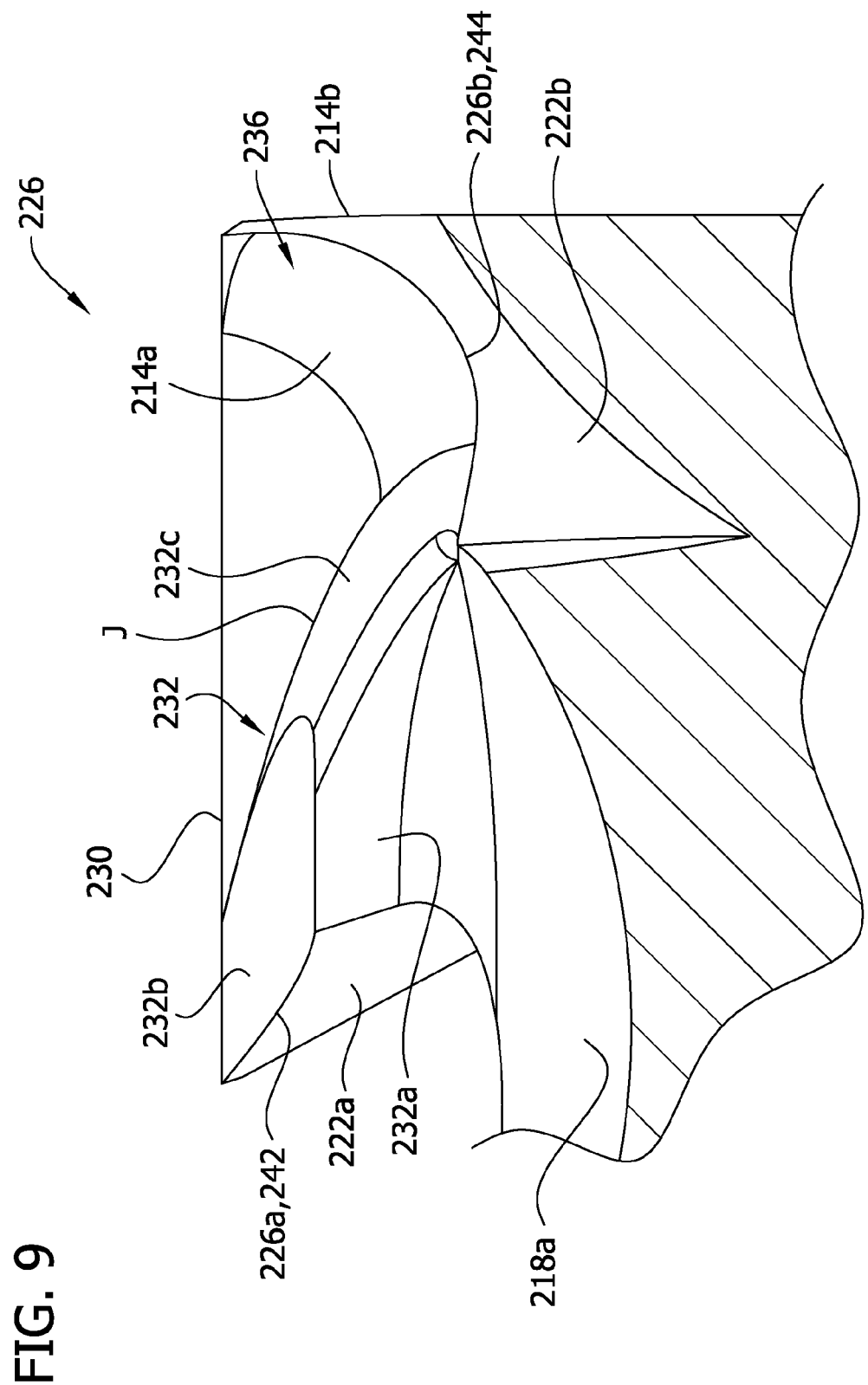
FIG. 9 is an enlarged fragmentary cross section taken through the line 9-9 in FIG. 7A.
Figure 11:
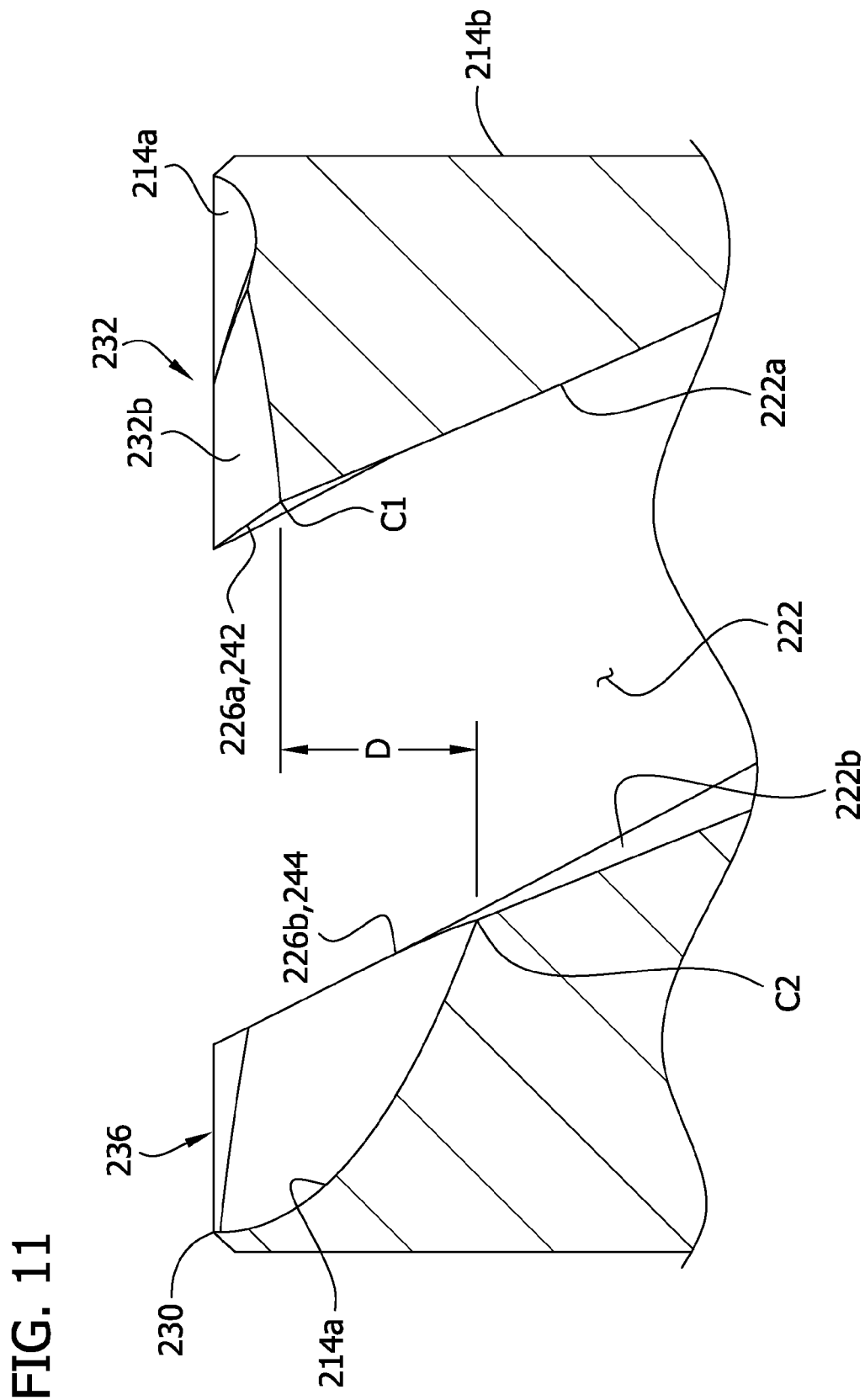
FIG. 11 is an enlarged fragmentary cross section taken through the line 11-11 in FIG. 7A.

Referring FIGS. 5, 7, and 7A, the cutter body 214 includes a central hub 218; a plurality of arcuate cutting elements, generally indicated at 220 (e.g., three cutting elements), each of which extends around a partial circumference of the hub; and a plurality of helical flutes (e.g., three flutes) 222, located between adjacent cutting elements. The flutes 222 each extend generally longitudinally through the cutter body and through the distal and proximal ends of the body 214. The hub 218 has recessed surface 218a (i.e., a central hub surface) at a central area of the distal end of the cutter body 214, and each cutting element 220 has an arcuate, distal cutting member, generally indicated at 226, partially surrounding the recessed surface of the hub at the distal end of the cutter body. The distal cutting members 226 may be formed integrally with the cutter body 214, or may be formed separately therefrom and secured thereto by suitable means. In the illustrated embodiment, the cutter 112 is configured for rotation in the direction indicated by arrow R (FIG. 7). As such, each distal cutting member 226 has a leading end 226a, a trailing end 226b, and an arc length extending between the leading and trailing ends. An arcuate cutting edge 230 of each cutting member 226 extends along the arc length of the arcuate cutting member 226, and is defined by the intersection or junction of an interior surface 214a and an exterior surface 214b of the cutter body 214 (FIGS. 9 and 11). As such, the arcuate cutting edges 230 are located generally at or adjacent a radially outer portion of the distal end of the cutter 112. The arcuate cutting edges 130 lie in a common cutting plane CP extending generally transverse to the longitudinal axis $LA_3$ of the cutter (FIG. 6).

As shown best in FIG. 7A, each arcuate cutting member 226 has a raised element, generally indicated at 232, located adjacent the leading end 226a thereof, and extending distally outward relative to the recessed hub surface 218a; and a clearance portion, generally indicated at 236, that is recessed from the raised element and extends from the raised element to the trailing end 226b of the cutting member. Each raised element 232 has an inner wall 232a extending distally from adjacent the recessed hub surface 218a, a distal wall 232b sloping proximally from adjacent the cutting edge 230 to the inner wall, and a trailing wall 232c extending from the distal wall toward the trailing end 226b of the cutting member 226. As explained below, in the illustrated embodiment the trailing wall 232c partially defines the clearance portion 236 of the cutting member 226. The entire distal wall 232b may adjacent to, but recessed longitudinally from, the corresponding arcuate cutting edge 230 so that the distal wall is spaced a minimum longitudinal distance from about 0.0010 to about 0.0050 inch (0.0025 to 0.0127 cm), including about 0.0010, about 0.0020, about 0.0030, about 0.0040 or about 0.0050 inch (0.0025, 0.0051, 0.0076, 0.0101, or 0.0127 cm), from the arcuate cutting edge.

In the illustrated embodiment, the trailing wall 232c of each raised element 232 gradually slopes proximally from the distal wall 232b to the trailing end 226b of the cutting member 226. The trailing wall 232c also tapers (i.e., gradually decreases) in radial width from the distal wall 232b to the trailing end 226b of the cutting member 226. As shown in FIG. 7A, the interior surface 214a of the cutting body 214 extends alongside the trailing wall 232c of the raised element 232 (and intersects the trailing wall at junction line J). Together, the interior surface 214a and the trailing wall 232c define the clearance portion 236, although it is understood that the clearance portion may be of other configurations. The interior surface 214a gradually increases in radial width from the distal wall 232b to the trailing end 226b of the cutting member 226. The rate in which the radial width of the interior surface 214a increases is generally commensurate with the rate in which the radial width of the trailing wall 232c decreases. The interior surface 214a is generally arcuate in cross section (e.g., generally cup-shaped from the arcuate cutting edge 230 to the junction line J).

Figure 5A:
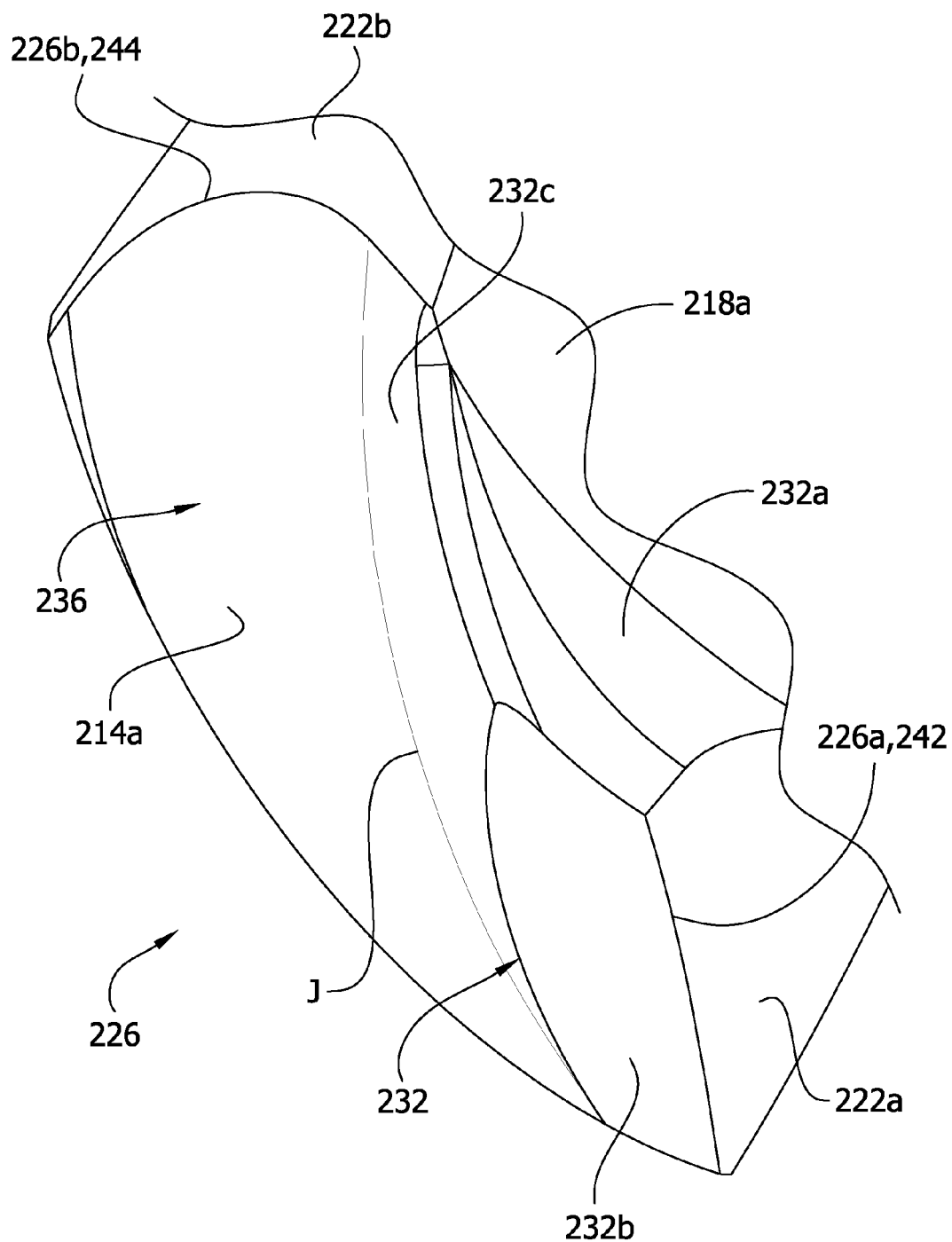
FIG. 5A is an enlarged, fragmentary view of FIG. 5, illustrating a cutting element of the cutter.
Figure 10:
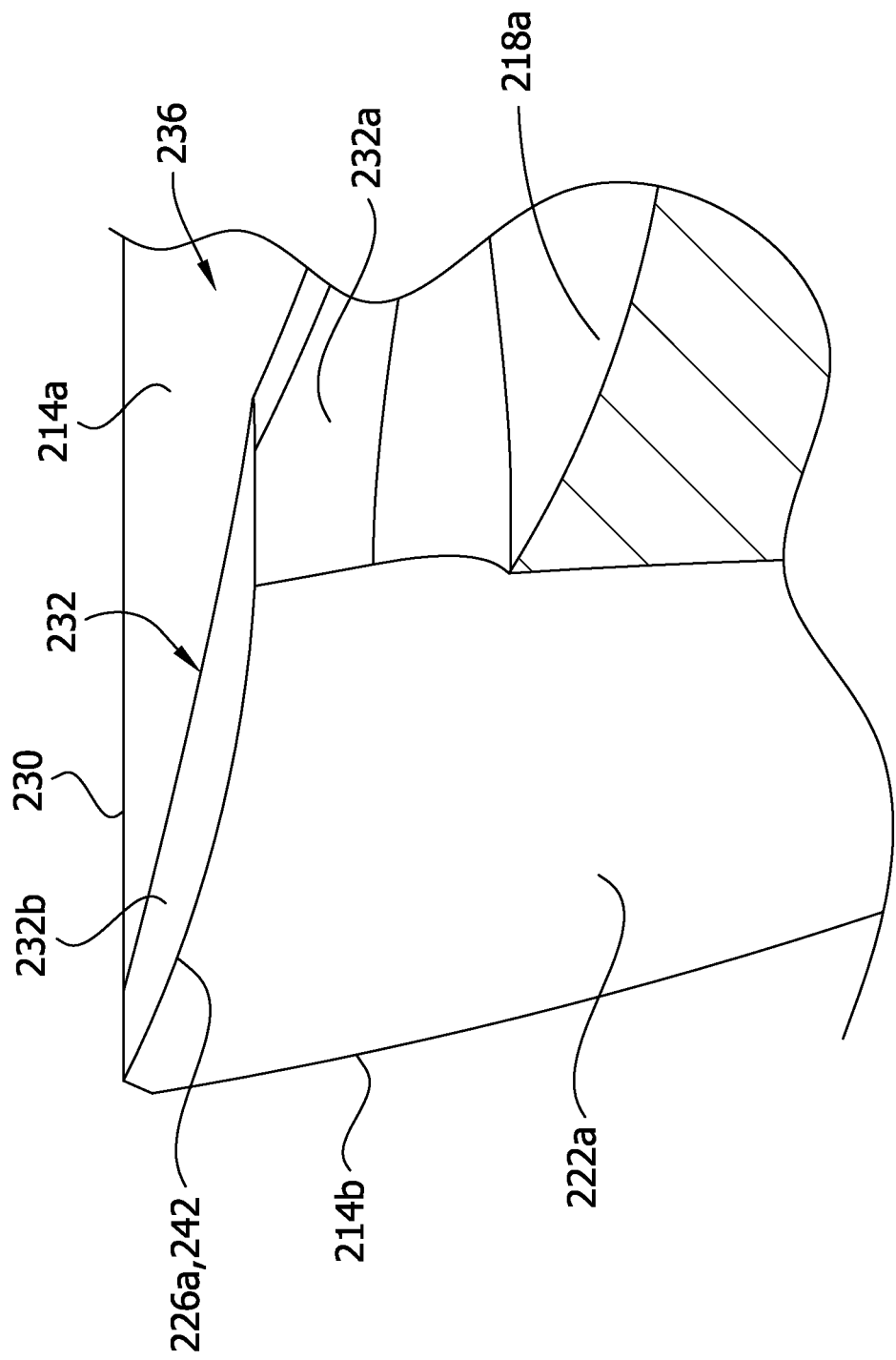
FIG. 10 is an enlarged fragmentary cross section taken through the line 10-10 in FIG. 7A.

As shown best in FIGS. 5A, 10, and 11, a leading cutting edge 242 of each raised element 232 is defined at the intersection of the distal wall 232b and an adjacent flute wall 222a partially defining the adjacent flute 222. In the illustrated embodiment, the leading cutting edge 242 is at the leading radial end 226a of the cutting member 226. A trailing edge 244 (FIGS. 5A, 7A, and 9) is defined at the intersection of the recessed clearance portion 236 and an adjacent flute wall 222b of one of the flutes 222, generally at the longitudinal end 226b. Due to the helical design of the flutes 222, the distal wall 232b may intersect the adjacent flute wall 222a at an acute angle (e.g., 60 degrees), whereby the leading cutting edge 242 is an acute edge, and the recessed clearance portion 236 may intersect the adjacent flute wall 222b at an obtuse angle (e.g., 120 degrees), whereby the trailing edge 244 is an obtuse edge. As seen best in FIGS. 7A and 11, the leading cutting edge 242 of a particular cutting element 220 generally opposes the trailing edge 244 of a corresponding cutting element that is on the opposite side of the associated flute 222. As explained below, at least a portion of the leading cutting edge 242 is more distal than the corresponding opposing trailing edge 244 to provide clearance for the leading cutting edge to engage tissue as the cutter is rotated about is longitudinal axis $LA_3$. For example, referring to FIG. 11 the respective centers C1, C2 of the leading cutting edge 242 and the trailing edge 244 may be spaced apart longitudinally a distance D at least about 0.001 in (0.0254 mm), or from about 0.001 in (0.0254 mm) to about 0.015 in (0.381 mm).

As set forth above, the cutter 112 is rotatable about its longitudinal axis $LA_3$ in the direction indicated by reference character R (FIG. 7). (This direction is generally clockwise when viewed from the proximal end of the cutter 112.) When the cutter 112 is deployed in its cutting position (e.g., FIG. 4) and the cutter is rotated about its longitudinal axis $LA_3$, the cutting elements 220 repeatedly pass through the cutting window 159 in a cyclical fashion and engage the tissue to be removed. In particular, with reference to cutting action of a single cutting element 220 as it is rotated about the longitudinal axis $LA_3$ of the cutter 112, the arcuate cutting edge 230 at the leading end 226a of the cutting element cuts through the tissue as the cutter rotates. Simultaneously, the leading cutting edge 242 of the raised element 232 cuts through the tissue as the cutter 112 rotates. In particular, the raised element 232 produces a hammer-like impact against the tissue to be removed as the cutter 112 is rotated. In the case where the tissue to be removed has brittle characteristics (e.g., has become calcified), the tissue will be crushed into smaller particles thereby facilitating its removal. Repeated rotation of cutter 112 will produce repeated hammer-like blows of the cutter raised elements 232 against the tissue to be removed. The removed material enters the flute 222 adjacent the raised element 232 that is engaging the tissue, and the removed tissue is moved proximally into the tissue-transport passage, where it can be picked up by the screw blade, in one example.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter comprising:
an elongate catheter body configured for insertion into a body lumen of a subject, the catheter body having opposite distal and proximal ends, and a longitudinal axis extending between the distal and proximal ends;
a rotatable cutter located generally at the distal end of the catheter body, the cutter having a proximal end, a distal end, and a longitudinal axis extending between the proximal and distal ends of the cutter, the cutter including
a central hub extending generally along the longitudinal axis of the cutter and having a circumference, the central hub having a central hub surface at a distal end of the central hub,
a plurality of flutes spaced apart from one another around the circumference of the central hub and extending through the distal end of the cutter and generally longitudinally along the cutter,
a plurality of arcuate cutting members at the distal end of the cutter, each arcuate cutting member having a leading end, a trailing end, and an arc length extending between the leading and trailing ends and partially surrounding the circumference of the hub, whereby each arcuate cutting member is spaced apart from an adjacent one of the arcuate cutting members by one of the flutes, each arcuate cutting member including
an arcuate cutting edge at a radially outer portion of the distal end of the cutter and extending along the arc length of the arcuate cutting member for cutting tissue as the cutter is rotated, wherein the arcuate cutting edges lie in a common cutting plane that extends generally transverse to the longitudinal axis of the cutter,
a raised element located adjacent the leading end of the arcuate cutting member and extending distally outward relative to the central hub surface, the raised element having a leading cutting edge at the leading end of the arcuate cutting member for cutting tissue as the cutter is rotated, and
a clearance portion that is recessed, relative to the longitudinal axis of the cutter, from the raised element and extends from the raised element to the trailing end of the arcuate cutting member to provide clearance for the leading cutting edge of an adjacent and opposing arcuate cutting member.

2. The tissue-removing catheter set forth in claim 1, wherein the flutes extend through proximal ends of the arcuate cutting members.

3. The tissue-removing catheter set forth in claim 2, wherein the flutes extend along the circumference of the central hub in a helical direction.

4. The tissue-removing catheter set forth in claim 3, further comprising a drive shaft extending longitudinally within the catheter body and operatively connected to the cutter for imparting rotation to the cutter.

5. The tissue-removing catheter set forth in claim 4, wherein the cutter includes a stem extending proximally from the central hub of the cutter, the drive shaft being connected to the stem.

6. The tissue-removing catheter set forth in claim 4, wherein the drive shaft includes an external helical thread for transporting removed tissue proximally within the catheter body.

7. The tissue-removing catheter set forth in claim 1, wherein the raised element of each arcuate cutting member has a distal wall, wherein the leading cutting edge of the raised element is defined at the intersection of the distal wall and an adjacent flute wall partially defining the adjacent flute.

8. The tissue-removing catheter set forth in claim 7, wherein the raised element of each arcuate cutting member has an inner wall extending distally from adjacent the central hub surface of the central hub.

9. The tissue-removing catheter set forth in claim 8, wherein the distal wall of each raised element is adjacent to and recessed proximally from the corresponding arcuate cutting edge.

10. The tissue-removing catheter set forth in claim 9, wherein the distal wall slopes proximally from adjacent the arcuate cutting edge to the inner wall.

11. The tissue-removing catheter set forth in claim 10, wherein the raised element of each arcuate cutting member has a trailing wall extending from the distal wall toward the trailing end of the arcuate cutting member, wherein the trailing wall slopes proximally from the distal wall toward the trailing end of the corresponding arcuate cutting member.

12. The tissue-removing catheter set forth in claim 11, wherein the trailing wall of each raised element tapers in radial width from the distal wall toward the trailing end of the corresponding arcuate cutting member.

13. The tissue-removing catheter set forth in claim 12, wherein each arcuate cutting member has a generally cup-shaped interior surface extending proximally from adjacent the arcuate cutting edge.

14. The tissue-removing catheter set forth in claim 13, wherein the interior surface intersects the trailing wall at a junction line, and wherein the interior surface increases in radial width from the distal wall toward the trailing end of the corresponding arcuate cutting member.

15. The tissue-removing catheter set forth in claim 7, wherein the flutes extend along the circumference of the central hub in a helical direction.

16. The tissue-removing catheter set forth in claim 15, wherein the distal wall of each raised element intersects said adjacent flute wall at an acute angle.

17. The tissue-removing catheter set forth in claim 16, wherein the distal wall of each raised element intersects said adjacent flute wall at an angle of 60 degrees.

18. The tissue-removing catheter set forth in claim 1, wherein the plurality of flutes consists of three flutes, and wherein the plurality of arcuate cutting members consists of three arcuate cutting members.

19. The tissue-removing catheter set forth in claim 1, wherein respective centers of the leading cutting edge of the raised element of one arcuate cutting member and a trailing edge of an adjacent arcuate cutting member and the trailing end of an adjacent arcuate cutting member are spaced apart a distance, relative to the longitudinal axis of the cutter, measuring from about 0.001 in (0.0254 mm) to about 0.015 in (0.381 mm).

20. A cutter for a catheter, the cutter having a proximal end, a distal end, and a longitudinal axis extending between the proximal and distal ends, the cutter comprising:
   a central hub extending generally along the longitudinal axis of the cutter and having a circumference, the central hub having a central hub surface at a distal end of the central hub;
   a plurality of flutes spaced apart from one another around the circumference of the central hub and extending through the distal end of the cutter and generally longitudinally along the cutter; and
   a plurality of arcuate cutting members at the distal end of the cutter, each arcuate cutting member having a leading end, a trailing end, and an arc length extending between the leading and trailing ends and partially surrounding the circumference of the hub, whereby each arcuate cutting member is spaced apart from an adjacent one of the arcuate cutting members by one of the flutes, each arcuate cutting member including
      an arcuate cutting edge at a radially outer portion of the distal end of the cutter and extending along the arc length of the arcuate cutting member for cutting tissue as the cutter is rotated, wherein the arcuate cutting edges lie in a common cutting plane that extends generally transverse to the longitudinal axis of the cutter,
      a raised element located adjacent the leading end of the arcuate cutting member and extending distally outward relative to the central hub surface, the raised element having a leading cutting edge at the leading end of the arcuate cutting member for cutting tissue as the cutter is rotated, and
      a clearance portion that is recessed, relative to the longitudinal axis of the cutter, from the raised element and extends from the raised element to the trailing end of the arcuate cutting member to provide clearance for the leading cutting edge of an adjacent and opposing arcuate cutting member.

21. A tissue-removing catheter comprising:
an elongate catheter body configured for insertion into a body lumen of a subject, the catheter body having opposite distal and proximal ends, and a longitudinal axis extending between the distal and proximal ends;
a rotatable cutter located generally at the distal end of the catheter body, the cutter having a proximal end, a distal end, and a longitudinal axis extending between the proximal and distal ends of the rotatable cutter, the rotatable cutter including
   a central hub extending generally along the longitudinal axis of the cutter and having a circumference, the central hub having a central hub surface at a distal end of the central hub,
   a plurality of flutes spaced apart from one another around the circumference of the central hub and extending through the distal end of the cutter and generally longitudinally along the cutter,
   a plurality of arcuate cutting members at the distal end of the cutter, each arcuate cutting member having a leading end, a trailing end, and an arc length extending between the leading and trailing ends and partially surrounding the circumference of the hub, whereby each arcuate cutting member is spaced apart from an adjacent one of the arcuate cutting members by one of the flutes, each arcuate cutting member including
      an arcuate cutting edge extending along the arc length of the arcuate cutting member for cutting tissue as the cutter is rotated,
      a raised element located adjacent the leading end of the arcuate cutting member and extending distally outward relative to the central hub surface, the raised element having a leading cutting edge at the leading end of the arcuate cutting member for cutting tissue as the cutter is rotated, and
      a clearance portion that is recessed, relative to the longitudinal axis of the cutter, from the raised element and extends from the raised element to the trailing end of the arcuate cutting member to provide clearance for the leading cutting edge of an adjacent and opposing arcuate cutting member,
   wherein the raised element of each arcuate cutting member has a distal wall, wherein the leading cutting edge of the raised element is defined at the intersection of the distal wall and an adjacent flute wall partially defining the adjacent flute, wherein the raised element of each arcuate cutting member has an inner wall extending distally from adjacent the central hub surface of the central hub, wherein the distal wall of each raised element is adjacent to and recessed proximally from the corresponding arcuate cutting edge, wherein the distal wall slopes proximally from adjacent the arcuate cutting edge to the inner wall, wherein the raised element of each arcuate cutting member has a trailing wall extending from the distal wall toward the trailing end of the arcuate cutting member, wherein the trailing wall slopes proximally from the distal wall toward the trailing end of the corresponding arcuate cutting member.

\* \* \* \* \*